US006623761B2

(12) United States Patent
Hassan

(10) Patent No.: US 6,623,761 B2
(45) Date of Patent: Sep. 23, 2003

(54) METHOD OF MAKING NANOPARTICLES OF SUBSTANTIALLY WATER INSOLUBLE MATERIALS

(76) Inventor: EmadEldin M. Hassan, Coventry House, Apt. B2 8048 Oxford Ave., Philadelphia, PA (US) 19111

( * ) Notice: Subject to any disclaimer, the term of this patent is extended or adjusted under 35 U.S.C. 154(b) by 0 days.

(21) Appl. No.: 09/748,803

(22) Filed: Dec. 22, 2000

(65) Prior Publication Data

US 2002/0119916 A1 Aug. 29, 2002

(51) Int. Cl.[7] .................................................. A61K 9/14
(52) U.S. Cl. ....................... 424/489; 424/490; 424/497; 424/9.4; 514/951
(58) Field of Search ................................ 424/489, 490, 424/497, 9.4; 514/951

(56) References Cited

U.S. PATENT DOCUMENTS

| 4,275,194 A | 6/1981 | Kato et al. |
|---|---|---|
| 4,826,689 A | 5/1989 | Violanto |
| 5,129,877 A | 7/1992 | Gallo et al. |
| 5,145,684 A | 9/1992 | Liversidge et al. |
| 5,399,363 A | 3/1995 | Liversidge et al. |
| 5,518,187 A | 5/1996 | Bruno et al. |
| 5,538,955 A | 7/1996 | De Rosa et al. |
| 5,560,932 A | 10/1996 | Bagchi et al. |
| 5,569,448 A | 10/1996 | Wong et al. |
| 5,571,536 A | 11/1996 | Eickhoff et al. |
| 5,573,749 A | 11/1996 | Illig |
| 5,573,783 A | 11/1996 | Desieno et al. |
| 5,580,579 A | 12/1996 | Ruddy et al. |
| 5,603,916 A | 2/1997 | Singh |
| 5,620,706 A | 4/1997 | Dumitriu et al. |
| 5,622,938 A | 4/1997 | Wong |
| 5,628,981 A | 5/1997 | Liversidge et al. |
| 5,665,330 A | 9/1997 | Wong |
| 5,716,642 A | 2/1998 | Bagchi et al. |
| 5,780,062 A | 7/1998 | Frank et al. |
| 5,803,966 A | 9/1998 | Kulshreshtha et al. |
| 5,836,970 A | 11/1998 | Pandit |
| 5,862,999 A | 1/1999 | Czekai et al. |
| 5,902,798 A | 5/1999 | Gouda et al. |
| 6,068,858 A | 5/2000 | Liversidge et al. |
| 6,120,789 A | 9/2000 | Dunn |
| 6,124,273 A | 9/2000 | Drohan et al. |
| 6,150,581 A | 11/2000 | Jiang et al. |

Primary Examiner—Christopher S. F. Low
Assistant Examiner—Chih-Min Kam
(74) Attorney, Agent, or Firm—John S. Child, Jr.

(57) ABSTRACT

This invention relates to a novel process of manufacture of nanoparticles of substantially water insoluble materials from emulsions. The emulsions have the ability to form a single liquid phase upon dilution of the external phase, instantly producing dispersible solid nanoparticles. The formed nanoparticles have average diameter of about 10 to 200 nm and are suitable for drug delivery and targeting of water insoluble therapeutic or diagnostic agents. Examples of such agents are methotrexate, progesterone, testosterone, prednisolone, and ibuprofen. Such agents can be used in a wide range of therapeutic and diagnostic treatments including treatment for cancer, hormonal therapy, and pain management.

20 Claims, No Drawings

METHOD OF MAKING NANOPARTICLES OF SUBSTANTIALLY WATER INSOLUBLE MATERIALS

FIELD OF THE INVENTION

This invention relates to nanoparticles of substantially water insoluble materials, methods of preparation, and use thereof. In particular, the invention relates to nanoparticles of therapeutic and diagnostic agents, method of preparation thereof, and pharmaceutically useful dispersions containing these nanoparticles. This invention further relates to methods of treatment using these nanoparticles.

BACKGROUND OF THE INVENTION

Nanoparticles of substantially water insoluble materials (i.e. materials that have water solubility of less than 0.1%) have a wide variety of applications, including therapeutic and diagnostic agents, paints, inks, dyes, and semiconductors. In most cases, performance of these nanoparticles dramatically improves as the nanoparticle size is reduced to 200 nanometers or less. Nanoparticles of therapeutic and diagnostic agents, in particular of a pharmaceutical compound ("drug") are customarily delivered with a solid or liquid carrier. Liquid containing nanoparticles such as emulsions, microemulsions and liposomes, however, usually suffer from the inherent physical instability of fluids resulting from globule dissociation. Solid polymeric or lipid nanoparticles have more structural stability, yet the rate of biodegradation of the nanoparticles and/or controlled release of the agent in the nanoparticles may not take place as intended, thereby adversely affecting optimal agent delivery and targeting. In addition, only a relatively small amount of the agent or drug can be encapsulated in fluid or solid carriers, requiring large, and sometimes impractical size dosages.

Carrier-free nanoparticles, made entirely of a water insoluble therapeutic agent or drug, have been introduced as an alternative solution for the above limitations and drawbacks. There are two major techniques described in the prior art, to produce solid drug nanoparticles. These techniques are known as wet grinding, and antisolvent precipitation. Other general techniques for nanoparticle formation, such as solvent evaporation and emulsion polymerization, are either not suitable or have not proved to be successful in making carrier-free drug nanoparticles.

Wet grinding involves the mechanical crushing of brittle crystalline drug particles, using hard beads made of glass, porcelain, zirconium oxide, or similar materials (of about 1–2 mm diameter), and aqueous solution of a hydrophilic material. The hydrophilic solution, which can be a surface active agent, surface modifier, or surface stabilizer, prevents aggregation or caking of the ground particles. An aggregate or a cake of drug particles is usually elastic in nature due to entrapped air or liquid within the void spaces between the particles and is not susceptible to further size reduction by bead bombardment. Accordingly, the wet grinding technique is not suitable for making nanoparticles from elastic materials. In addition, because the hard grinding beads can erode during grinding, remnants of the grinding beads can become incorporated in the nanoparticles, causing particle contamination.

The liquid antisolvent technique involves dissolving the water insoluble compound in suitable organic solvent, and diluting that solution with a non-solvent, which is miscible in the solution. The non-solvent neither dissolves the compound nor causes its precipitation from the original solvent. Solid nanoparticles are then generated by carefully controlling the precipitation step by addition of an antisolvent liquid (usually water or an aqueous solution). Since the formation of the nanoparticles is solely dependent on the diffusion of totally miscible liquids under non-structural geometry, or boundaries, resultant particle size, surface, and shape are critically sensitive to minimal changes in the precipitation conditions. The drawbacks of this process are that it is difficult to control and requires considerable preparation. Recently, the use of a supercritical fluid antisolvent, such as pressurized carbon dioxide, gained considerable attention because of the simpler clean up and recovery of the nanoparticles. However, supercritical fluid precipitation requires high pressure, which greatly increases the difficulty in controlling the process.

It would be desirable to have an alternative method for the preparation of substantially water insoluble nanoparticles without the drawbacks of the prior art methods.

SUMMARY OF THE INVENTION

According to one aspect, this invention provides a method of making nanoparticles of substantially insoluble water compounds and more specifically, nanoparticles of a water insoluble pharmaceutical compound (or "drug") from an emulsion in which a solution of said material forms the globules of the dispersed phase. These emulsions are readily transformed into a single uniform liquid phase, in which nanoparticles of the diagnostic or therapeutic agent are suspended, upon further dilution with the external or continuous phase. The resulting dispersed solid nanoparticles are generally less than 200 nm average diameter.

An advantageous feature of this invention is that therapeutic or diagnostic nanoparticles so produced can be utilized for intravascular injections to treat or diagnose local or systemic diseases. Another advantageous feature is that extravascular injections containing these particles can provide controlled release of the drug at the site of injection for prolonged drug effects, and minimize multiple dosing. Yet another advantage of this invention is improved drug transport across absorption barriers such as mucosal gastrointestinal barriers, nasal, pulmonary, ophthalmic, and vaginal membranes, and other distribution barriers, such as the blood—tissue and blood—tumor barriers of various organs and tissues. For example, anti-cancer nanoparticles of less than 50 nm diameter can migrate through the compromised, more permeable vascular bed to reach tumor tissues. Once the nanoparticles are inside the tumor tissue they will provide local cytotoxic action against the tumor cells. In the case of highly protected organs such as the brain, with its tight vascular bed surrounding the normal tissues, drug nanoparticles will preferentially concentrate in the tumor tissue, with minimal or no toxicity to the healthy brain tissue. A further advantage of this invention is the improved oral bioavailability of poorly absorbed drugs.

DETAILED DESCRIPTION OF THE INVENTION AND PREFERRED EMBODIMENTS

The formation of oil-in-water or water-in-oil emulsions is a well-known process. Emulsions suitable for generating nanoparticles of therapeutic or diagnostic agent in accordance with this invention comprise a dispersed or internal phase in which the agent is totally soluble, an appropriate emulsifier, e.g., a surfactant, and a continuous or external phase with limited solubilizing affinity to the dispersed phase.

While not intending to be confined by a particular theory, the nanoparticles described above appear to be formed by the following mechanism. After emulsification, the system comprises generally spherically shaped globules of agent surrounded by a protective sheath of emulsifier molecules. Those globules are dispersed throughout a bulk of the external phase. The emulsion will be intact as long as the protective sheath is intact and the external phase cannot dissolve the molecules of agent in the dispersed phase. Further dilution of the emulsion with the external phase will cause the sheath to become thinner, allowing the external phase to dissolve some or all of the internal phase globules. The dissolution of the internal phase globules in the external phase results in the production of nanometer-sized particles of the therapeutic or diagnostic agent. Aside from the novel procedure by which these nanoparticles are formed, a fundamental and unique feature of this invention is that precipitation of solid drug nanoparticles from the emulsion globules provides ultimate control over nanoparticle size because the resulting nanoparticles are less than or at least similar to the globule size of the initial emulsion.

Unlike the wet grinding technique, this invention can be practiced with a wide variety of therapeutic and diagnostic agents in either the crystalline or the amorphous state. Therapeutic and diagnostic agents with the following utilities can be employed in this invention:

| | |
|---|---|
| antineoplastic | hormone |
| antimicrobial | hormone antagonist |
| antiviral | cardiac glycoside |
| anticoagulant | immunosuppressant |
| antihypertensive | beta-blocker |
| antihistamine | $H_2O$-insol. vitamin |
| antimalarial | hypoglycemic agent |
| contraceptive | hyperglycemic agent |
| antiepileptic | analgesic |
| depressant | tranquilizer |
| antidepressant | mood-altering drug |
| adrenocortical steroid | |

Examples of agents that are useful include substances capable of treating or preventing an infection systemically or locally, as for example, antibacterial agents such as penicillin, cephalosporins, bacitracin, tetracycline, doxycycline, quinolines, clindamycin, and metronidazole; antiparasitic agents such as quinacrine, chloroquine and vidarabine; antifungal agents such as nystatin; antiviral agents such as acyclovir, ribarivin and interferons; anti-inflammatory agents such as hydrocortisone and prednisone; analgesic agents such as salicylic acid, acetaminophen, ibuprofen, naproxen, piroxicam, flurbiprofen and morphine; local anesthetics such as lidocaine, bupivacaine, benzocaine, and the like; immunogens (vaccines) for stimulating antibodies against hepatitis, influenza, measles, rubella, tetanus, polio and rabies; peptides such as leuprolide acetate (an LH-RH agonist), nafarelin and ganirelix.

Also useful is a substance or metabolic precursor thereof, which is capable of promoting growth and survival of cells and tissues or augmenting the functioning of cells, as for example, a nerve growth promoting substance such as a ganglioside, a nerve growth factor, and the like; a hard or soft tissue growth promoting agent such as fibronectin (FN), human growth hormone (HGH), a colony stimulating factor, bone morphogenetic protein, platelet-derived growth factor (PDGF), insulin-derived growth factor (IGF-I, IGF-II), transforming growth factor-alpha (TGF-a), transforming growth factor-β (TGF-β), epidermal growth factor (EGF), fibroblast growth factor (FGF) and interleukin-1 (IL-1); an osteoinductive agent or bone growth promoting substance such as bone chips and demineralized freeze-dried bone material; and antineoplastic agents such as methotrexate, 5-fluoroacil, adriamycin, vinblastine, cisplatin, tumor-specific antibodies conjugated to toxins and tumor necrosis factor.

Other useful substances include hormones such as progesterone, testosterone, and follicle stimulating hormone (FSH) (birth control, fertility-enhancement), insulin metal complexes and somatotropins; antihistamines such as diphenhydramine and chlorpheneramine; cardiovascular agents such as digitalis glycosides, papaverine and streptokinase; anti-ulcer agents such as cimetidine, famotidine and isopropamide iodide; vasodilators such as theophylline, B-adrenergic blocking agents and minoxidil; central nervous system agents such as dopamine; antipsychotic agents such as risperidone, olanzapine; narcotic antagonists such as naltrexone, maloxone and buprenorphine.

Preferred therapeutic and diagnostic agents are water insoluble anticancer drugs such as carmustine (BCNU), antiviral drugs such as azidothymidine (AZT) and other nucleosides, HIV Protease inhibitors such as saquinavir and retinovir immune-modulating agents such as cyclosporine, natural and synthetic hormones and hormone regulators such as contraceptives. Light imaging contrast materials for x-ray imaging such as iodinated materials (Iodepamide derivatives), Magnetic Resonance imaging contrast agents such as metal oxides (Iron $Fe_3O_4$ and $Fe_2O_2$) and markers for diagnostic nuclear medicine used in scintegraphy as radio-labeled Technetium sulphur or Technetium oxide. Other preferred therapeutic agents are steroidal and non-steroidal anti-inflammatory agents such as hydrocortisone, prednisolone, ketoprofen, celecoxib and ibuprofen. Further preferred therapeutic agents are centrally acting medicines such as antiseptics, antidepressants and sedatives and cardiovascular drugs such as anti-hypertensives and blood lipid lowering agents. Particularly preferred therapeutic agents are water insoluble anti-cancer drugs, hormones, analgesics, cardiovascular, antimicrobial or anti-viral agents. This technique is also suitable for immune modulators and drugs that are soluble in dilute acids or bases. Methotrexate is a preferred drug substance that is soluble in dilute alkaline solutions.

Once the principle of the invention is understood, people experienced in the field can select suitable emulsion systems for each agent. Preferred emulsion systems are triethyl citrate-water, dimethylsulphoxide-triglyceryl cabroate and ethyl citrate-water. Alkaline or acidic aqueous solutions comprising triethyl citrate are especially useful for emulsion systems for agents of pH-selective solubility. Acids in liquid form, such as hydrochloric, acetic, phosphoric, and lactic acids are preferred for acid soluble agents. Ammonium hydroxide, triethanolamine and ethylenediamine are preferred for alkali-soluble agents.

The choice of a suitable emulsifier or a combination of emulsifiers can readily be made by those in the field.

Surfactants

Surfactants which may be used for this purpose have preferably HLB value of 1 to about 20. Examples of them are as follows:

(a) Reaction products of natural or hydrogenated vegetable oils, and ethylene glycol; i.e., polyoxyethylene glycolated natural or hydrogenated vegetable oils: for example polyoxyethylene glycolated natural or hydrogenated castor oils. Surfactants commercialized under the trade names Cremophor RH-40, Cremophor RH60, Cremophor EL, Nikkol HCO-40 and Nikkol HCo-60 may be used in the composition according to the present invention. Cremophor RH40 and Cremophor El are preferred.

(b) Polyoxyethylene sorbitan fatty acid esters: e.g., mono- and tri-lauryl, palmityl, stearyl and oleyl esters; e.g. products of the trade name "Tween," which includes polyoxyethylene sorbitan mono-laurate (Tween), polyoxyethylene sorbitan mono-palmitate (Tween 40), polyoxyethylene sorbitan mono-oleate (Tween 80), etc. depending on the kind of fatty acid. Tween 20 and Tween 40 can be used preferably in the composition according to the present invention.

(c) Polyoxyethylene fatty acid esters: for example, polyoxyethylene stearic acid esters of the type known and commercially available under the trade name Myrj as well as polyoxyethylene fatty acid esters known and commercially available under the trade name "Cetiol HE."

(d) Polyoxyethylene-polyoxypropylene co-polymers: e.g. of the type known and commercially available under the trade names "Pluronic" and "Emkalyx."

(e) Polyoxyethylene-polyoxypropylene block co-polymers: e.g. of the type known and commercially available under the trade name "Poloxamer."

(f) Dioctylsuccinate, dioctylsodiumsulfosuccinate, di-[2-ethylhexyl]-succinate or sodium lauryl sulfate.

(g) Phospholipids, in particular lecithins: especially, soybean lecithin.

(h) Surfactants such as non-ionic polyoxyethylene fatty acid derivatives, in particular, polyoxyethylene sorbitan fatty acid esters (spans) such as sorbitan sesquiolate are preferred for use as emulsifiers.

Emulsification is usually performed by applying mechanical force to break down the internal phase liquid into small globules, in the range of 10 to 200 nm, more preferably less than 200 nm, and even more preferably less than 50 nm in diameter, and molecules of surfactant molecules forming a barrier between the globules and the bulk of the external liquid. Such mechanical force can be applied by mechanical stirring, ultrasonic probes, or by passing the emulsion components through narrow space, as in the case of colloidal mills, or through narrow tubes, valves or orifices. The preferred emulsification technique is passing the liquid through narrow tubes.

To obtain solid nanoparticles, the emulsion should be diluted to allow total miscibility of the liquid dispersed phase inside the continuous phase. The miscibility of the liquid dispersed phase is accompanied by the formation of the nanoparticles from the resulting one liquid phase system. The dilution step can be carried out with either an additional portion of the continuous phase solution or a liquid that is miscible with both the dispersed and continuous phases. Diluting with the same continuous phase solution is preferred.

Separation of nanoparticles can be performed using dialysis, filtration, centrifugation, or other known techniques. Nanoparticles can then be formulated into a suspension dosage form according to standard procedures in the art for injection or non-injection use. Nanoparticles can also be dried and reconstituted prior to use.

The composition of this invention enables sustained, continuous delivery of drugs, medicaments and other biologically active agents to tissues adjacent to or distant from an administration site. The biologically-active agent is capable of providing a local or systemic biological, physiological or therapeutic effect. For example, the agent may act to control infection or inflammation, enhance cell growth and tissue regeneration, control tumor growth or enhance bone growth, among other functions.

The nanoparticles of the invention can be administered using a pressure applicator such as injection into tissue through a syringe, needle, pump or similar article or by techniques known for delivering medication to parts of the human body, such as orally in a suspension, hard or soft capsules, or by topical application on the skin, to the eye, or into a mucous membrane or body cavity.

The nanoparticles of therapeutic or diagnostic agent are administered in an amount effective to provide the desired level of biological, physiological, pharmacological and/or therapeutic effect. The active agent may stimulate or inhibit a biological or physiological activity. There is generally no critical upper limit on the amount of the agent being administered. The concentration of the bioactive agent should not be so high that the composition has a consistency that inhibits its delivery to the administration site by the desired method. The lower limit of the amount of agent will depend on the activity of the agent and the period of time desired for treatment. The agent is gradually released by dissolution of the nanoparticles.

For further examples of agents that may be used in the present invention, see U.S. Pat. No. 5,324,519, the entire disclosure of which is incorporated by reference herein.

The invention is further described below with reference to various specific and preferred embodiments and techniques. The following examples are presented for illustration purposes only and are not to be taken as limiting the present invention in any way.

EXAMPLE 1

Progesterone nanoparticles with average diameter of 12.6 nm, as determined by dynamic light scattering technique, were produced as follows:

180 milligrams of progesterone were dissolved in five milliliters of triethylcitrate by heating at 60° C. Five grams of Chromophore EL (Sigma, St. Louis, Mo.) used as the emulsifier were mixed with forty (40) milliliters of water at 60° C., and the mixture was added to the progesterone solution. An oil-in-water emulsion was made by passing the above mixture through a high-pressure homogenizer (Avestin, Inc., Ottawa, ON, Canada). Ten milliliters of the formed emulsion were immediately diluted with fifty milliliters of water while stirring. Progesterone nanoparticles were separated by centrifugation.

EXAMPLE 2

Methotrexate nanoparticles with an average diameter of 198 nm, as determined by dynamic light scattering technique, were produced according to this invention. Fifty milligrams of methotrexate were dissolved in five milliliters of 0.1% ammonium hydroxide aqueous solution with a pH value adjusted to 9.0 with acetic acid. Five grams of sorbitan sesquioleate (Arlacel 83, ICI Americas Inc.) was then mixed with forty milliliters of triethylcitrate at 50° C. and the mixture was added to the methotrexate solution. A water-in-oil emulsion was made by passing the above mixture through a high-pressure homogenizer (Avestin, Inc., Ottawa, ON, Canada). Ten milliliters of the formed emulsion were immediately diluted with fifty milliliters of triethylcitrate containing 0.1% (v/v) acetic acid while stirring. Methotrexate nanoparticles were separated by centrifugation.

EXAMPLE 3

Testosterone nanoparticles with an average diameter of 32 nm, as determined by dynamic light scattering technique, were produced as follows:

Two hundred milligrams of testosterone were dissolved in five milliliters of triethyl citrate. Five grams of Chromophore El were then mixed with forty milliliters of distilled water at 50° C. and the mixture was added to the testosterone solution. An oil-in-water emulsion was made by passing the above mixture through a high-pressure homogenizer (Avestin, Inc., Ottawa, ON, Canada). Ten milliliters of the formed emulsion were immediately diluted with fifty milliliters of water while stirring. Nanoparticles were separated by centrifugation.

EXAMPLE 4

Ibuprofen nanoparticles with an average diameter of 49 nm, as determined by dynamic light scattering technique, were produced as follows:

Five hundred milligrams of ibuprofen were dissolved in five milliliters of triethyl citrate. Five grams of Chromophore El were then mixed with forty milliliters of distilled water at 50° C. and the mixture was added to the ibuprofen solution. An oil-in-water emulsion was made by passing the mixture through a high-pressure homogenizer (Avestin, Inc., Ottawa, ON, Canada). Ten milliliters of the formed emulsion were immediately diluted with fifty milliliters of water while stirring. Nanoparticles were separated by centrifugation.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

I claim as my invention:

1. A method of making nanoparticles of a substantially water insoluble therapeutic agent selected from the group consisting of progesterone, testosterone, methotrexate and ibuprofen, said method comprising the steps of:
   (a) dissolving said therapeutic agent in a first liquid component of an emulsion system to form a solution;
   (b) adding to the solution a second liquid component of an emulsion system and a surfactant functioning as an emulsifier to form a mixture;
   (c) applying mechanical force to the mixture of (b) in order to transform the mixture into an emulsion comprising a continuous phase and a dispersed phase in which the continuous phase comprises the second liquid component of the emulsion system and the surfactant, and the dispersed phase comprises globules of the therapeutic agent dissolved in the first liquid component, said globules having a diameter of between 10 and 200 nm; and
   (d) treating the emulsion formed in step (c) with an additional amount of the second component thereby transforming the emulsion into a liquid-solid suspension, whereby the solid phase comprises nanoparticles of the agent.

2. The method as claimed in claim 1, wherein the therapeutic agent is ibuprofen.

3. The method as claimed in claim 1, wherein the second liquid component is water.

4. The method as claimed in claim 1, wherein the globules formed in step (c) have a diameter of less than 50 nm.

5. The method as claimed in claim 1, wherein in the emulsion formed in step (c) the surfactant forms a barrier between the continuous phase and the dispersed phase.

6. The method as claimed in claim 1, wherein the two components in the emulsion system are triethyl citrate and water.

7. The method as claimed in claim 1, said method comprising an additional step of separating the nanoparticles from the liquid in the suspension by passing the suspension through a porous barrier which retains the nanoparticles but not the liquid.

8. The method as claimed in claim 7, wherein the barrier is a semi-permeable membrane.

9. The method as claimed in claim 1, wherein the components of the emulsion system are an alkaline aqueous solution and triethyl citrate.

10. The method as claimed in claim 1, wherein the components of the emulsion system are an acidic aqueous solution and triethyl citrate.

11. The method as claimed in claim 1, wherein the components are ethyl citrate and water.

12. The method as claimed in claim 1, wherein the therapeutic agent is progesterone.

13. The method as claimed in claim 1, wherein the therapeutic agent is testosterone.

14. The method as claimed in claim 1, wherein the therapeutic agent is methotrexate.

15. A method for making nanoparticles of a substantially water insoluble material selected from a hormone, an anti-neoplastic agent, and an anti-inflammatory agent, said method comprising the steps of:
   (a) dissolving said material in a first liquid component of an emulsion system to form a solution;
   (b) adding to the solution a second liquid component of an emulsion system and an emulsifier to form a mixture and applying force to the mixture in order to transform the mixture into an emulsion comprising a continuous phase and a dispersed phase in which the continuous phase comprises the second liquid component of the emulsion system, and the dispersed phase comprises globules of the material dissolved in the first liquid component, said globules having a diameter of between 10 and 200 nm; and
   (c) treating the emulsion formed in step (b) with an additional amount of a liquid miscible with the first and second components, thereby transforming the emulsion into a liquid-solid suspension, whereby the solid phase comprises nanoparticles of the material.

16. The method as claimed in claim 15, wherein the substantially water insoluble material is selected from the group consisting of progesterone, testosterone, hydrocotisone, prednisolone, ketoprofen, celecoxib, ibuprofen and methotrexate.

17. The method of making nanoparticles according to claim 15, wherein the force applied in step (b) is a mechanical force.

18. The method of making nanoparticles according to claim 15, wherein the force applied to the mixture of step (b) is applied by passing the emulsion through a narrow space.

19. The method of making nanoparticles according to claim 15, wherein the force is applied by means of passing the emulsion through a narrow passage of an article selected from the group consisting of a colloidal mill, tube and valve.

20. The method of making nanoparticles according to claim 15, wherein the force is applied by means of a mechanical device selected from the group consisting of mechanical stirring and ultrasonic probe.

* * * * *